(12) United States Patent  
Shigekawa et al.

(10) Patent No.: US 7,961,379 B2
(45) Date of Patent: Jun. 14, 2011

(54) PUMP PROBE MEASURING DEVICE AND SCANNING PROBE MICROSCOPE APPARATUS USING THE DEVICE

(75) Inventors: Hidemi Shigekawa, Tsukuba (JP); Osamu Takeuchi, Tsukuba (JP)

(73) Assignee: Japan Science and Technology Agency, Saitama (JP)

( * ) Notice: Subject to any disclaimer, the term of this patent is extended or adjusted under 35 U.S.C. 154(b) by 214 days.

(21) Appl. No.: 12/516,800

(22) PCT Filed: Nov. 28, 2007

(86) PCT No.: PCT/JP2007/072988
§ 371 (c)(1), (2), (4) Date: May 28, 2009

(87) PCT Pub. No.: WO2008/066090
PCT Pub. Date: Jun. 5, 2008

(65) Prior Publication Data
US 2010/0088787 A1    Apr. 8, 2010

(30) Foreign Application Priority Data
Nov. 29, 2006 (JP) .................................. 2006-322662

(51) Int. Cl.
*G01Q 20/02* (2010.01)
*G01N 21/00* (2006.01)
(52) U.S. Cl. .............. 359/331; 359/326; 850/6; 850/21; 250/310; 250/306; 73/800
(58) Field of Classification Search .................. 359/331, 359/326; 850/6, 21; 250/310, 306; 73/800
See application file for complete search history.

(56) References Cited

U.S. PATENT DOCUMENTS
5,748,318 A   5/1998  Maris et al.
(Continued)

FOREIGN PATENT DOCUMENTS
JP   10-233544 A     9/1998
JP   2000-515624 A   11/2000
WO   03-046519 A1    6/2003

OTHER PUBLICATIONS
International Search Report (ISR) for PCT/JP2007/072988, citing U.S. Patent Nos. 1-8, U.S. Patent Application Publications Nos. 1-3, Foreign Patent Documents Nos. 1-3, and Non-Patent Literature Nos. 2-3.

(Continued)

*Primary Examiner* — Nikita Wells
(74) *Attorney, Agent, or Firm* — Chen Yoshimura LLP (57) ABSTRACT

A pump probe measuring device (1) includes an ultrashort optical pulse laser generator (11) for generating a first ultrashort optical pulse train, which becomes a pump light, and a second ultrashort optical pulse train, which becomes a probe light, a delay time adjusting unit (15) for adjusting a delay time between ultrashort optical pulse trains, a first pulse picker and a second pulse picker (13, 14) for accepting each of the first and the second ultrashort optical pulse trains and allowing only one pulse to be transmitted at an arbitrary repetition periodicity, thus reducing the effective repetition frequency of the optical pulses, a delay time modulation unit (10) for periodically changing a position through which pulses are transmitted by the first and the second pulse pickers (13, 14), an irradiation optical system (16) for applying pump light and probe light to a sample (19), a measuring unit (20) for detecting probe signals from a sample (19), and a lock-in amplifier (18).

11 Claims, 9 Drawing Sheets

U.S. PATENT DOCUMENTS

| | | |
|---|---|---|
| 5,959,735 A | 9/1999 | Maris et al. |
| 6,111,416 A * | 8/2000 | Zhang et al. ............... 324/244.1 |
| 6,175,416 B1 | 1/2001 | Maris et al. |
| 6,208,421 B1 | 3/2001 | Maris et al. |
| 6,271,921 B1 | 8/2001 | Maris et al. |
| 6,321,601 B1 | 11/2001 | Maris et al. |
| 6,400,449 B2 | 6/2002 | Maris et al. |
| 7,002,149 B2 * | 2/2006 | Shigekawa et al. ........... 250/307 |
| 7,508,853 B2 * | 3/2009 | Harter et al. .................... 372/30 |
| 2001/0028460 A1 * | 10/2001 | Maris et al. ................... 356/432 |
| 2002/0018210 A1 | 2/2002 | Maris |
| 2005/0035288 A1 | 2/2005 | Shigekawa et al. |

OTHER PUBLICATIONS

Kensuke Ogawa, "Femtosecond spectrum sampling technology and its applications to nonlinear spectroscopy of semiconductors", Technical report of IEICE LQE, vol. 98, No. 342, Oct. 21, 1998, pp. 59-64.

Bartels et al., "Femtosecond time-resolved optical pump-probe spectroscopy at kilohertz-scan-rates over nanosecond-time-delays without mechanical delay line" Applied Physics Letters, vol. 88, Issue 4, Jan. 25, 2006, ID. 041117.

Translation of PCT/ISA/237 of PCT/JP2007/072988 with IB338 and IB373.

* cited by examiner

PUMP PROBE MEASURING DEVICE AND SCANNING PROBE MICROSCOPE APPARATUS USING THE DEVICE

TECHNICAL FIELD

The present invention relates to a pump probe measuring device for measuring and analyzing ultrafast physical phenomena and a scanning probe microscope apparatus using this measuring device. More specifically, the invention relates to a pump probe measuring device employing rectangular-wave-based delay time modulation using pulse pickers, and a scanning probe microscope apparatus using this measuring device.

BACKGROUND ART

As the almost only means for measuring a phenomenon that occurs in an extremely short time period of the order of picosecond (ps) or femtosecond (fs), the pump probe method using an ultrashort pulse laser beams is known. The pump probe method is available in various embodiments. All the embodiments measure probe signals as a function of delay time, which is the duration from the excitation of a sample by pump light to the detection of the state of the sample by probe light. Ultrafast response of the sample to photoexcitation can thus be measured while achieving high time resolution of the order of femtosecond.

Since the intensity of signals obtained by this measurement method is low in general, modulation measurement is performed to pick up desired signals from noise. The modulation of the pump light intensity was the most common modulation measurement method. This method has achieved good results in researches in which time-resolved measurement is conducted to measure the reflectance of probe light.

Depending on measurement environment, however, modulation of high-intensity pump light causes the sample temperature to increase and decrease repetitively, which may adversely affect the measurement. This problem has been a concern in a series of researches to create a so-called time-resolved scanning probe microscope capable of achieving ultimate resolution in both time and space regions by combining the pump probe method and a scanning probe microscope.

On the other hand, as a method that does not modulate light intensity, the delay time modulation method is known. The conventional delay time modulation method changes optical path length by physically moving the position of a mirror placed on the pump light path to adjust delay time. Consequently, with the delay time modulation method, the limited capacity of a driving mechanism for physically transferring the mirror restricts the transfer distance of the mirror, causing delay time setting range to be limited to 1 ns or shorter, and delay time modulation range to 100 ps or shorter. In addition, since modulation cannot be realized with a large-amplitude and high-frequency, modulation frequency is limited to 20 Hz or lower, for example. Thus, the measurement of a phenomenon having relaxation time of several hundred ps or longer, for example, cannot be carried out. Furthermore, the mechanical transfer of the mirror position vibrates an optical bench, causing the optical axis to deviate and eventually decreasing measurement accuracy.

Moreover, since the signal intensity is proportional to the modulation amplitude in this delay time modulation method, modulation amplitude must be increased to measure small and gradual relaxation processes.

However, increasing modulation amplitude decreases modulation frequency and thus increases noise amplitude. In addition, since output signals are the average value over the entire modulation amplitude, time resolution decreases. Furthermore, since differentiated signals are measured with this delay time modulation method in principle, the absolute value of signals cannot be found, which makes physical interpretation difficult.

Meanwhile, taking advantage of the feature that it does not cause increase and decrease of the temperature of samples and the measurement system, this conventional delay time modulation method was combined with a scanning probe microscope into a delay-time-modulated scanning probe microscope, which has accomplished certain results.

On the other hand, a new delay time modulation method was designed recently. It has two laser oscillators oscillating at repetition frequencies slightly differing from each other and are used for each laser as a pump light and a probe light. In this case, the delay time is scanned from zero to the repetition period at high speed at the modulation frequency equivalent to the difference between the two repetition frequencies. By recording probe signals in synchronization with the frequency equivalent to the difference between the above repetitive frequencies and averaging the obtained values, the measurement can be performed easily even in a large delay time region without mechanically changing the mirror position, and the absolute signal values can thus be measured. Furthermore, this method is superior to the previously mentioned methods in that modulation frequency can be increased.

Nonpatent literature 1: A. Bartels, Appl. Phys. Lett. 88, 041117 (2006)

DISCLOSURE OF THE INVENTION

Problems to be Solved by the Invention

However, in order to take advantage of this new delay time modulation method, a probe signal detector with relatively wide bandwidth is required. If the bandwidth of the probe signal detector is narrow, the modulation frequency, which is the difference between the repetitive frequencies of two lasers, must be decreased to extremely low level. This increases noise level. In addition, since this new delay time modulation method requires two expensive laser oscillators, which must be oscillated synchronized, the overall cost of the measurement apparatus increases.

Under such circumstances, an inexpensive pump probe measuring device featuring wide measurement range and high detection sensitivity, and applicable to special measurement environment including combined use with a scanning probe microscope, has been much sought after.

The object of the present invention is to solve the above problems in time-resolved measurement using pulse lasers applicable to the femtosecond region, by providing a pump probe measurement device for measuring ultrafast physical phenomena for analyses capable of measuring faint signals stably and highly accurately over a wide measurement range, including phenomena having short or long relaxation time, without modulating the intensity of irradiated light, namely without being affected by heat, and a time-resolved scanning probe microscope apparatus using that device.

Means for Solving the Problem

To achieve the above object, the present invention provides a pump probe measuring device including: an ultrashort optical pulse laser generator for generating a first ultrashort optical pulse train, which becomes a pump light, and a second ultrashort optical pulse train, which becomes a probe light; a delay time adjusting unit for adjusting a delay time of the first and the second ultrashort optical pulse trains; a first pulse picker and a second pulse picker for reducing effective repetition frequency of optical pulses by accepting each of the first and second ultrashort optical pulse trains and transmitting only one pulse at an arbitrary repetition frequency; a delay time modulating unit for periodically changing a position through which optical pulses are transmitted by the first and the second pulse pickers; a measuring unit for detecting probe signals from a sample equipped with an irradiation optical system for applying the pump light and probe light to the sample; and a lock-in detecting unit for performing phase-sensitive detection of probe signals from the sample at a modulation frequency of the delay time modulation unit, wherein the first or the second pulse picker changes the position through which optical pulses are transmitted, thus changing the delay time between the optical pulse that is transmitted through said second pulse picker and the optical pulse that is transmitted through said first pulse picker.

According to the above configuration, by periodically changing the timing at which the pulse picker transmits and blocks the pump light and the probe light pulses, which are continuously generated by the ultrashort optical pulse laser generator, the delay time can be changed by large amount at high speed.

Since the present invention does not employ modulation of pump light intensity, repetitive temperature change does not occur; even samples sensitive to temperature change during measurement are not affected adversely. Samples in a broad range of fields can thus be measured.

According to the present invention, by transmitting and blocking optical pulses generated from laser equipment using pulse pickers in order to transmit optical pulses at relatively long repetition period, a physical phenomenon having relaxation time longer than the repetition period of the laser equipment, 1 µs for example, can be measured easily. Since measurement can be made even in a very large delay time region, exceeding the optical pulse repetition frequency, a probe signal in excited state and that after complete relaxation of the sample can be compared. As a result, not only the differential value but also the absolute value of the signal can be obtained, which facilitates physical interpretation. Furthermore, since there is no need to shift the mirror position over a long distance, the optical axis of output laser beams does not deviate, thus ensuring high measurement accuracy.

According to the present invention, since the modulation amplitude can be increased, the signal intensity increases to several to several tens times that of the conventional delay time modulation method. In addition, a high modulation frequency allowed in the present invention decreases the noise intensity down by half to approximately one tenth of the conventional method, for example, when a long relaxation period of several picoseconds or longer is measured. This allows the so-called signal-to-noise (S/N) ratio to be increased by approximately 50 to 100 times that of the conventional method.

In the above configuration, the pulse pickers preferably include Pockels cells and light polarizers to transmit and block arbitrary optical pulses. The delay time modulation unit preferably includes: a photosensor for detecting optical pulses generated by the ultrashort optical pulse laser generator; a counting means for counting pulse signals from the photosensor; a delaying means to be connected to the counting means; and a driving means for the pulse pickers. According to this configuration, arbitrary pulses can be transmitted or blocked quite easily.

In the above configuration, the ultrashort optical pulse laser generator can include a laser source comprising a titanium-sapphire laser oscillator. In this configuration, since laser pulses having, for example, wavelength of 800 nm and pulse width of 25 fs can be generated at the repetition frequency of approximately 100 MHz, ultrashort optical pulse laser can be obtained easily.

If the delay time adjusting unit includes an optical system that adjusts optical path length using movable mirrors, delay time can be adjusted using a delay time adjusting unit similar to a conventional one. In addition, since the mirror need not be transferred over a long distance, the optical axis of the pulse light applied to a sample rarely deviates, and as a result measurement accuracy increases.

If the ultrashort optical pulse laser generator includes an ultrashort optical pulse laser source and an optical device that divides the ultrashort optical pulses generated by the ultrashort optical pulse laser source into two optical paths to form pump light and probe light, only one ultrashort optical pulse laser device is needed as a light source, which ensures simple configuration and reduces overall device cost.

In a configuration in which the ultrashort optical pulse laser generator is equipped with two ultrashort optical pulse laser sources that emit light in the same cycles, and the ultrashort optical pulses generated at each ultrashort optical laser source are made to enter corresponding pulse pickers as the pump light and the probe light respectively, there is no need to branch light in order to feed it to two pulse pickers. Consequently, the intensity of the optical pulse applied to the sample can be enhanced, and the phase of the pump light and probe light can be shifted easily. If the two ultrashort optical pulse laser sources have different wavelengths, the pump light and the probe light can be made to have different wavelengths. Furthermore, if a synchronous oscillation control mechanism is provided for the two laser devices, by setting the phase of oscillating the pump light and probe light as required, the delay time up to the repetition period can be set easily. Consequently, since delay time can be adjusted by two ultrashort optical pulse laser sources and pulse pickers, the delay time adjusting unit, which is required when only one ultrashort optical pulse laser source is used, can be omitted.

When a cavity dumper is used as an ultrashort optical pulse laser source, by decreasing the repetition frequency of the optical pulses coming from the ultrashort optical pulse laser source, the intensity of each optical pulse can be increased, which allows the repetition frequency to be decreased without significantly decreasing the average intensity. When the operating frequency of the pulse pickers is limited to approximately 1 MHz, the optical intensity of the pump light and the probe light can be increased.

The above measuring unit preferably includes an optical system for irradiating the surface of the sample with the pump light and the probe light, and another optical system for measuring the intensity of reflected probe light, wherein the intensity of the reflected probe light is output as probe signals. According to this configuration, the change in reflectance on the surface of the sample, which occurs when the surface of the sample excited by the pump light becomes relaxed, can be observed as the change in the intensity of reflected probe light.

A scanning probe microscope apparatus according to the present invention is equipped with one of the previously mentioned pump probe measuring devices. The measuring unit further comprises a scanning tunneling microscope for measuring local physical properties at the position where the pump light and the probe light are applied, allowing probe signals obtained by the scanning tunneling microscope to be output.

A measuring device according to the present invention is equipped with one of the previously mentioned pump probe measuring devices as one of its components.

In the above configuration, a delay-time-modulated scanning probe microscope apparatus having time resolution of the order of fs can be achieved to observe the process of excitation by the pump light and that of relaxation on the surface of the sample with high spatial resolution of the order of angstrom or nanometer. Furthermore, the measuring device equipped with the pump probe measuring device according to the present invention can be achieved.

Effect of the Invention

In the field of the time-resolved measurement using pulse laser including the fs region, the present invention provides the pump probe measuring device for measuring and analyzing ultrafast physical phenomena, as well as the time-resolved scanning probe microscope apparatus using this measuring device, to measure the very weak signals highly accurately and stably over a wide measurement range, including phenomena having short and long relaxation time, without modifying the intensity of the light to be applied.

DESCRIPTION OF THE REFERENCE NUMERALS 1, 30, 40: Pump probe measuring device
10, 10A, 10B: Delay time modulation unit
11, 31, 32: Laser source
12: Branch optical system
12a: Half mirror
12b: Reflecting mirror
13: First pulse picker
13a, 14a: Electro-optic element
13b, 14b: Light polarizer
14: Second pulse picker
15: Delay time adjusting unit
15a: Movable mirror
16: Irradiation optical system
16a, 16b, 16d: Reflecting mirror
16c: Objective lens
17: Photosensor
18: Lock-in amplifier
19, 53: Sample
20: Measuring unit
21: Photosensor
22: Counting means
23, 24: Delaying means
25, 26: Driving means
33: Synchronous oscillation control unit
41: Cavity dumper
50: Scanning probe microscope apparatus
51: Irradiation optical system
51a: Half mirror
51b, 51c: Reflecting mirror
51d: Objective lens
52: Scanning tunneling microscope
52a: Probe
52b: Preamplifier
P1: Pump pulse light
P2: Probe pulse light Best Modes for Carrying Out the Claimed Invention Hereinafter, the present invention will be described in detail with reference to certain embodiments thereof illustrated in the drawings. In Figures, the same marks and symbols are used for identical or corresponding members.

Figure 1:
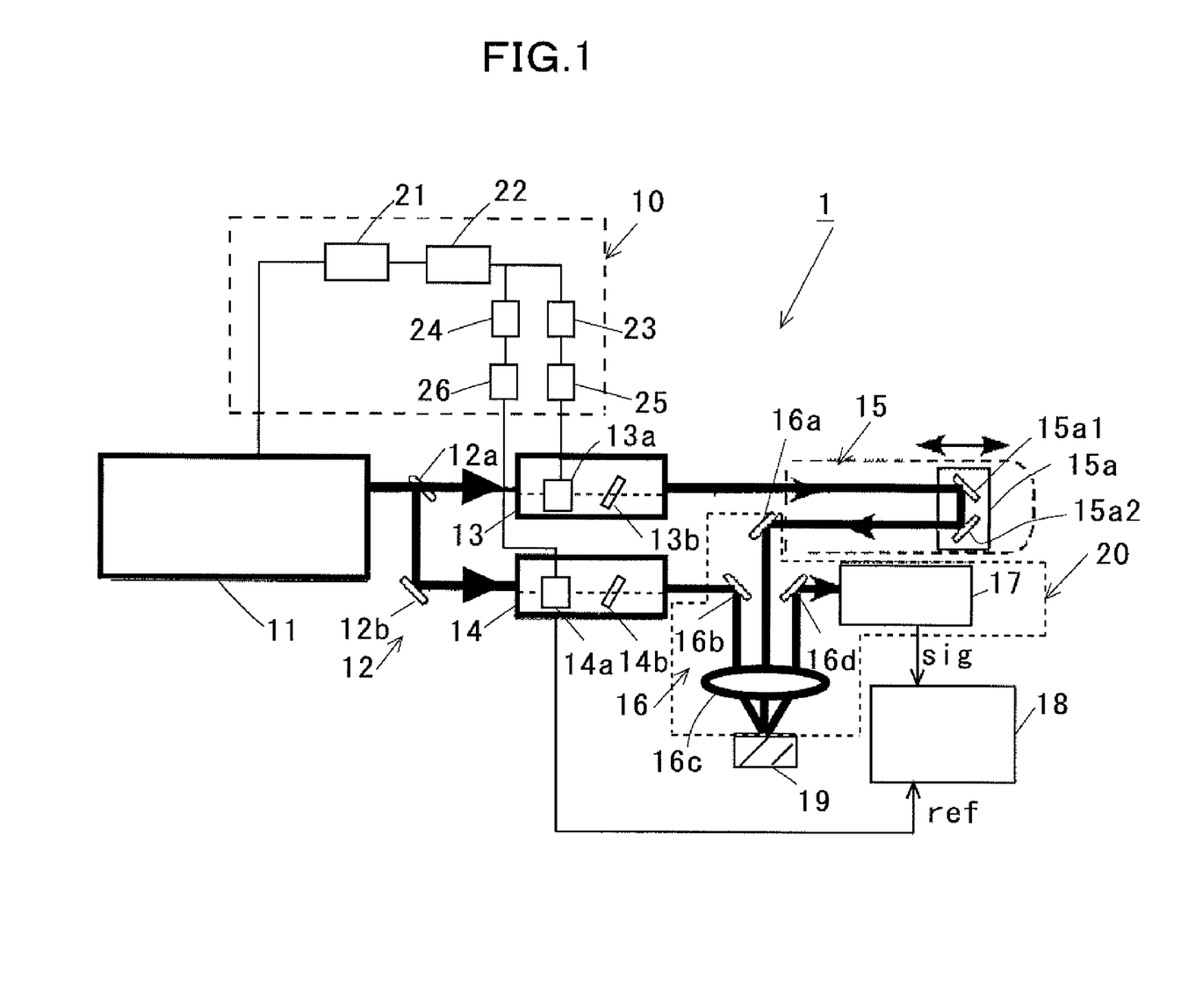
FIG. 1 is a block diagram illustrating the configuration of a first embodiment of a delay-time-modulated pump probe measuring device according to the present invention.

First, a delay-time-modulated pump probe measuring device relating to a first embodiment of the present invention will be described. FIG. 1 shows the configuration of a first embodiment of a delay-time-modulated pump probe measuring device according to the present invention. In FIG. 1, a delay-time-modulated pump probe measuring device 1 includes: an ultrashort optical pulse laser generator including a laser source 11 for generating a first ultrashort optical pulse train, which becomes pump light, and a second ultrashort optical pulse train, which becomes probe light; a branch optical system 12; two pulse pickers, namely a first pulse picker 13 and a second pulse picker 14; a delay time modulation unit 10 for periodically changing the position at which optical pulses are transmitted by the pulse pickers 13 and 14; a delay time adjusting unit 15; and an irradiation optical system 16, in addition to a measuring unit 20 for detecting probe signal from a sample 19 to be measured, and a lock-in detection unit 18 to be connected to the measuring unit 20.

The laser source 11 is a femtosecond pulse laser source, for example. Specifically, a titanium sapphire laser oscillator capable of generating laser pulses having wavelength of 800 nm, time width of approximately 25 fs at the repetition frequency of approximately 100 MHz, and average luminance of approximately 1 W, can be used.

The branch optical system 12 includes a half mirror 12a placed diagonally on the outgoing optical path of the laser pulses coming from the laser source 11. The laser pulses from the laser source 11 can be branched into a light transmitted through and a light reflected by the half mirror 12a.

Here, the light transmitted through the half mirror 12a is used as a pump light, whereas the light reflected by the half mirror 12a is used as a probe light. These may be reversed. Following description assumes that the transmitted light is used as the pump light, and the reflected light is used as the probe light.

In the Figure, the branch optical system 12 includes a reflecting mirror 12b placed on the reflected light path, which guides the reflected light into the second pulse picker 14.

The pulse pickers 13 and 14 include a first pulse picker 13, to which the pump light from the branch optical system 12 is introduced, and a second pulse picker 14, to which the probe light from the branch optical system 12 is introduced. The pulse pickers 13 and 14 selectively transmit, at an arbitrary period, only one pulse among laser pulse trains coming in at the repetition frequency as high as 100 MHz for example, and block the rest of the pulses. It is preferable to set the intensity ratio of the transmitted light to the blocked light as sufficiently high as 300:1 to 1,000:1.

The first pulse picker 13 and the second pulse picker 14 may be of the same configuration, but various configurations can also be selected on condition that each of them can extract a single light pulse. In the case shown in the Figure, each of the pulse pickers 13 and 14 includes electro-optic elements 13a and 14a, which rotates a polarization of the optical pulse by a voltage application, and light polarizers 13b and 14b placed on the output side of the electro-optic elements 13a and 14a. In the case of the Figure, a light polarizer 13b is placed on the output side, but the light polarizers can also be placed on both input and output sides of the electro-optic element 13a. If acousto-optic devices are used instead of electro-optic elements 13a and 14a to constitute the pulse pickers 13 and 14, light polarizers 13b and 14b are unnecessary. The electro-optic elements 13a and 14a are driven by the delay time modulation unit 10, which will be described later, to perform high-speed switching of the order of nanosecond. In order to transmit pulses with sufficiently high repetition rate, it is preferable that operating frequency of up to 1 MHz can be selected. Consequently, a Pockels cell can be used as each of the pulse pickers 13 and 14 and it may block 99 pulses out of 100 and transmit the remaining one pulse.

This allows the effective repetition frequency of pulses coming from the laser source 11 to decrease from 100 MHz to 1 MHz, and the average laser intensity from 1 W to 10 mW. The timing of transmission of optical pulses by the pulse pickers 13 and 14 will be described later by referring to FIG. 2.

The delay time modulation unit 10 periodically changes the selection position of the light pulses through the pulse pickers 13 and 14. For example, the delay time modulation unit 10 as shown in FIG. 1 includes: a photosensor 21 for detecting optical pulses generated from the ultrashort optical pulse laser generator 11; a counting means 22 for counting pulse signals coming from the photosensor 21; a first delaying means 23 and a second delaying means 24 to be connected to the counting means 22; and driving means 25 and 26 for driving the pulse pickers 13 and 14. The first and the second delaying means 23 and 24 may be placed on only one side. If the pulse pickers 13 and 14 are Pockels cells, the driving means 25 and 26 are high-voltage power supply devices.

A pin photodiode, an avalanche photodiode, or a photomultiplier having a fast response capability, for example, can be used as the photosensor 21, to ensure that it can respond to the optical pulses from the ultrashort optical pulse laser generator. The counting means 22 and the first and second delaying means 23 and 24 can be composed of pulse circuits using transistors, integrated circuits, microcomputers, etc., on condition that they can periodically change the selection position of the light pulses which transmit through the pulse pickers 13 and 14. If signals coming from the fast photosensor 21 is used as a clock signal, a microcomputer or a field programmable integrated circuit, i.e. a complex programmable logic device (CPLD), can be used to constitute the counting means 22 and the first and the second delaying means 23 and 24 for driving an optical shutter such as an electro-optic element to be used for the pulse pickers 13 and 14.

In the case shown in the Figure, the delay time adjusting unit 15 is composed of an optical system of a known configuration that adjusts the optical path length using a movable mirror 15a. The movable mirror 15a can be a pair of reflecting mirrors placed at the angle of 45 degrees against the incident light axis. A light coming in along the incident light axis is reflected by one of the reflecting mirrors 15a1 in the direction perpendicular to the incident light axis, hits the other reflecting mirror 15a2, and is reflected by the other reflecting mirror 15a2 in the direction parallel to the incident direction.

The position of the movable mirror 15a can be adjusted in the direction of the optical axis of the pump light pulses transmitted through the first pulse picker (pump pulse light). If the movable mirror 15a is transferred to right, the optical path length becomes longer, whereas if it is transferred to left, the optical path length becomes shorter.

Consequently, the delay time of the pump pulse light with respect to the probe light pulses (probe pulse light) can be set as any preferred time by moving the movable mirror 15a. For example, if the movable range of the optical path length is approximately 30 cm, the delay time between the probe pulse light and the pump pulse light can be set within the 0 to 1 ns range.

In the case shown in the Figure, the measuring unit 20 includes the irradiation optical system 16 and a photosensor 17 for detecting probe signals from the sample 19. The irradiation optical system 16 includes an objective lens 16c, which is placed near the surface of the sample 19, a reflecting mirror 16a for guiding the pump pulse light from the delay time adjusting unit 15 to the surface of the sample 19, a reflecting mirror 16b for guiding the probe pulse light from the second pulse picker 14 to the surface of the sample 19, and a reflecting mirror 16d for guiding the probe pulse light reflected on the surface of the sample 19 to the photosensor 17. Thus, these configurations allow pump pulse light and probe pulse light to focus on the surface of the sample 19. At that time, the pump pulse light reaches the sample 19 first, and immediately after that, the probe pulse light is reflected on the surface of the sample 19.

Probe signals reflected on the surface of the sample 19 enter the photosensor 17, reflected by the reflecting mirror 16d, and thus the reflectance of the surface of the sample 19 can be measured at the time when the precise delay time has elapsed after the pump pulse light is irradiated. A Si pin photodiode can be used as the photosensor 17, for example.

The lock-in detecting means can be composed of a lock-in amplifier 18. The lock-in detecting means is used to perform modulation measurement to ensure accuracy of measurement, because the delay time-dependent component (see "sig" in FIG. 1) of the reflected light intensity measured by the photosensor 17 is extremely small compared with the fluctuation of the light intensity of the laser source 11. The lock-in amplifier 18 performs a phase-sensitive detection of the signals measured by the photosensor 17 using the modulation frequency of the delay time modulation performed with the first and the second pulse pickers 13 and 14, which will be described later by referring to FIG. 2, as a reference signal (see "ref" in FIG. 1), thus enhancing measurement accuracy.

The features of the present invention include the pulse pickers 13 and 14 and the delay time modulation unit 10, which change periodically the selection positions of the light pulses which transmit through the pulse pickers 13 and 14. The operation of the delay time modulation unit 10 will be described below by referring to FIG. 2.

Figure 2:
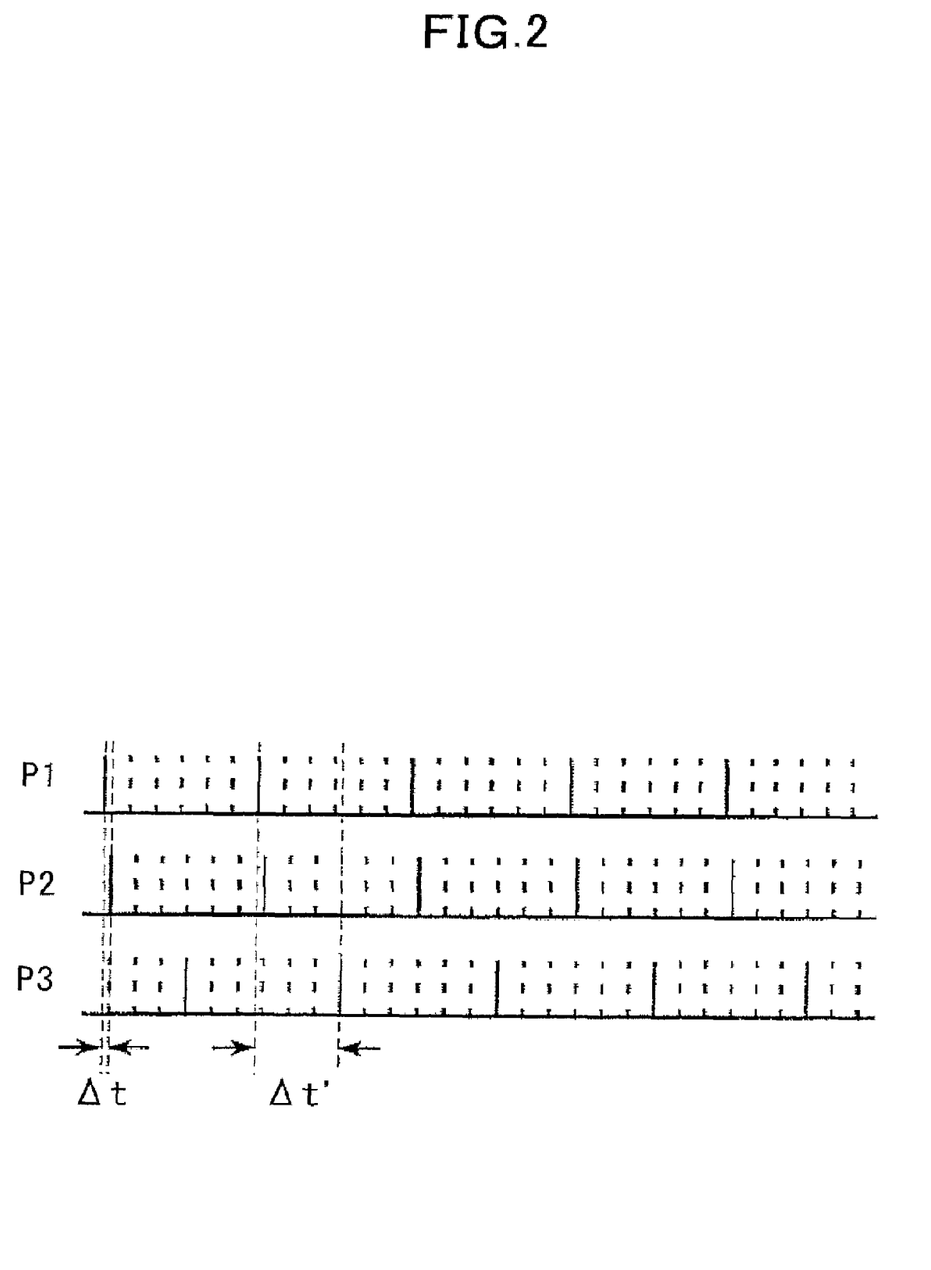
FIG. 2 is a chart illustrating the change with time of optical intensity of the pump pulse light and the probe pulse light reaching the surface of a sample with the measuring device in FIG. 1.

FIG. 2 is a chart illustrating the optical intensity of the pump pulse light P1 and probe pulse light P2 at the time when both reach the surface of the sample 19. The abscissa axis of the chart represents time, whereas the ordinate axis represents optical intensity. Since the pump pulse light P1 and the probe pulse light P2 are laser pulses from the laser source 11 having repetition frequency of approximately 100 MHz, each laser intensity remains at zero most of the time, and increases to a very high level for a time period as short as 25 fs only.

Consequently, the pump pulse light P1 and the probe pulse light P2 are illustrated as a comb-shaped chart as shown in FIG. 2.

If the repetition frequency of the laser pulses output from the laser source 11 is 100 MHz, the time interval between pulses is 10 ns both for the pump pulse light P1 and the probe pulse light P2. This time interval is expressed as the gap between dotted lines in FIG. 2. Only one pulse out of 100 pulses is transmitted and the remaining pulses are blocked by the operation of the pulse pickers 13 and 14. For convenience sake, one out of every 6 pulses is transmitted, and remaining 5 are blocked in FIG. 2. The transmitted light is expressed in a solid line, whereas the blocked light is expressed in dotted line.

If delay time caused by the delay time adjusting unit 15 is expressed as $-\Delta t$, the probe pulse light P2 lags behind the pump pulse light P1 by delay time $\Delta t$. At this time, the optical intensity measured by the photosensor 17 is proportional to the reflectance $R(\Delta t)$ of the sample at the time precisely $\Delta t$ after the excitation by the pump pulse light P1.

Figure 3:
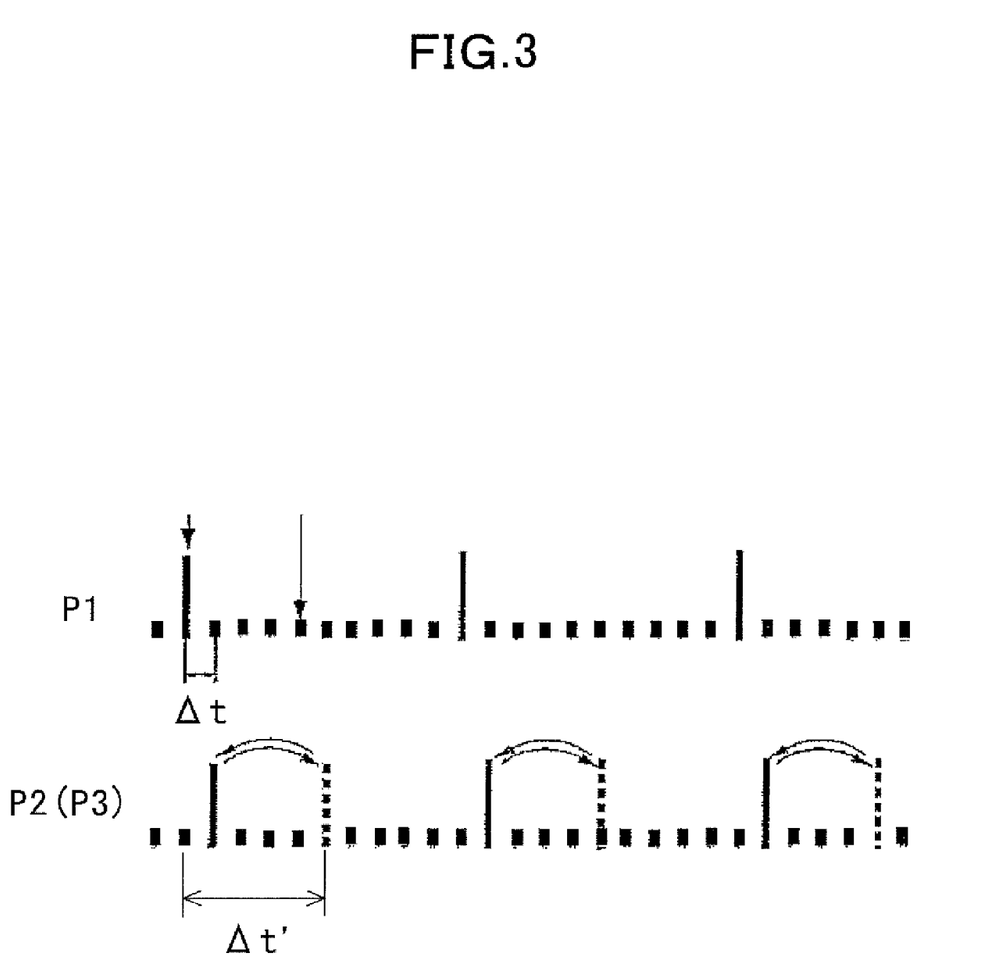
FIG. 3 is a chart illustrating the change of delay time of the pump pulse light and the probe pulse light in FIG. 2 caused by pulse pickers.

If the timing when the second pulse picker 14 transmits a pulse is delayed by the period for 3 pulses as shown by P3 in FIG. 2, the actual delay time is calculated to be $\Delta t' = \Delta t + 3 \times 10$ (ns), which demonstrates that the delay time can be increased instantaneously to a very large value. At this time, the optical intensity measured by the photosensor 17 is proportional to the reflectance $R(\Delta t')$ of the sample. If the state as shown by P2 and P3 in FIG. 2 is repeated periodically as shown in FIG. 3 by controlling the second pulse picker 14, thus changing the passing position of the probe pulse light, the signal measured by the photosensor 17 oscillates periodically between $R(\Delta t)$ and $R(\Delta t')$. The lock-in amplifier 18 performs the phase-sensitive detection of this signal, with the modulation frequency used as a reference signal, which allows the difference between $R(\Delta t)$ and $R(\Delta t')$ to be measured.

Since the delay time is modulated sinusoidally in the conventional delay time modulation method, the signals obtained by modulation measurement are expressed as average slope of R over the entire modulation amplitude region (between $\Delta t$ and $\Delta t'$). On the contrary, the delay time modulation method according to the present invention allows the delay time to be modulated into a precisely rectangular waveform, and the obtained signal is exactly in proportion to the difference between $R(\Delta t)$ and $R(\Delta t')$, namely $R(\Delta t) - R(\Delta t')$.

Figure 4:
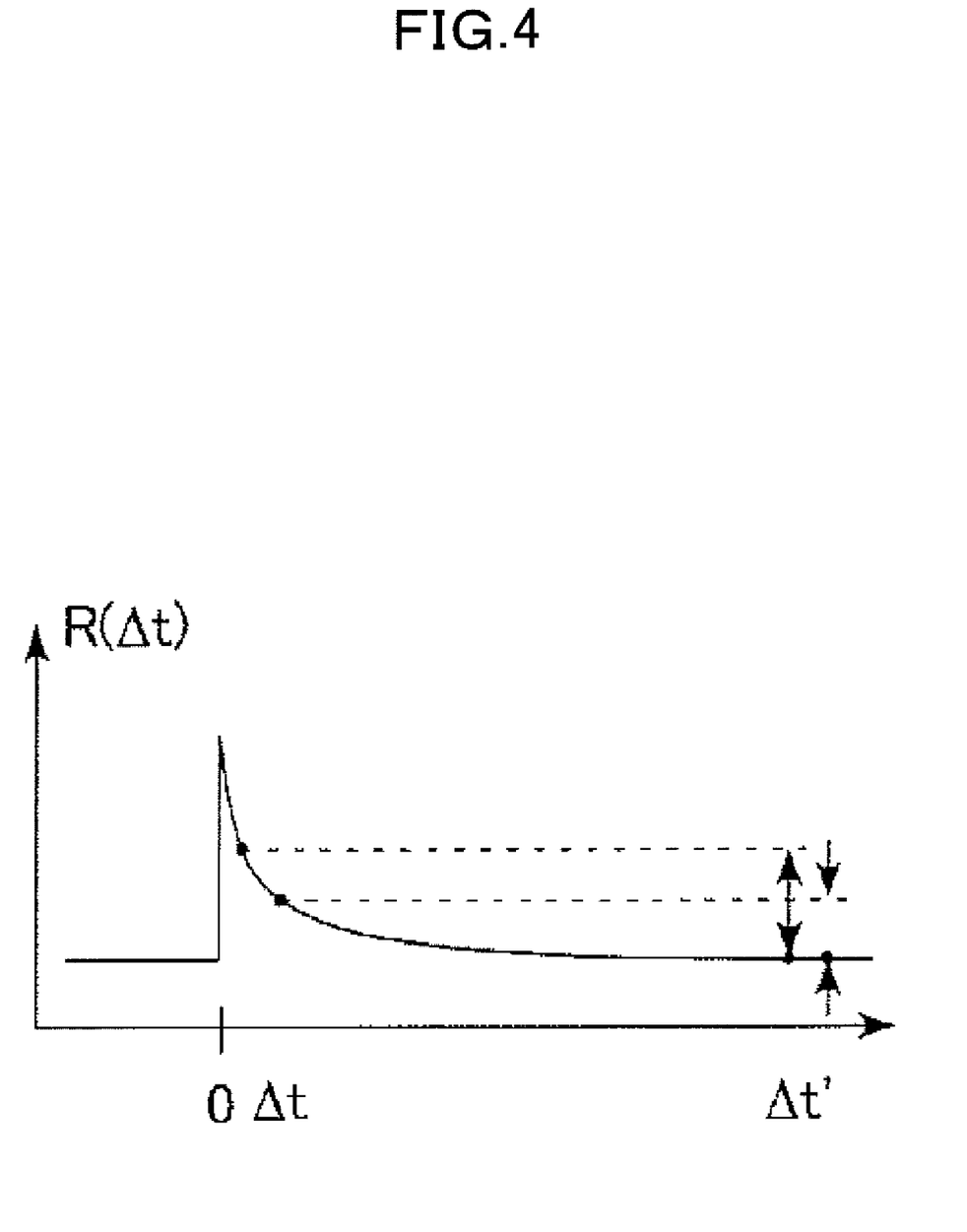
FIG. 4 is a chart illustrating a relaxation process of measured signals of a sample after being excited by the pump pulse light with the measuring device in FIG. 1.

This gives a very advantageous point as described below. Generally speaking, as shown in FIG. 4, the state of a sample after being excited by the pump light approaches a certain value after going through a relaxation time as short as several picoseconds to several nanoseconds. In ultrafast measurement, the amplitude and the duration of the relaxation time are targets of measurement.

In this embodiment, if a value approximately half the pulse repetition period after pulse picking is adopted as delay time $\Delta t'$ as shown in FIG. 2, $\Delta t'$ can take a very large value compared with the relaxation time of the sample 19. Since $\Delta t'$ is approximately 0.5 μs, for example, $R(\Delta t')$ is considered to represent the state of the sample 19 after the completion of relaxation, namely zero point of the signal. At this time, the difference between $R(\Delta t)$ and $R(\Delta t')$ measured in this embodiment, namely $R(\Delta t) - R(\Delta t')$, is equal to $R(\Delta t)$ itself, and thus the absolute value of the delay time-dependent component of reflectance can be obtained.

In addition, if the delay time between the pump pulse light P1 and the probe pulse light P2 is changed by the delay time adjusting unit 15 in FIG. 1, not only $\Delta t$ but also $\Delta t'$ changes. However, as described previously, if a sufficiently large value is selected as $\Delta t'$, $R(\Delta t')$ can be regarded as a constant, whereas $R(\Delta t)$ reflects fast relaxation process immediately after the excitation of the sample. Consequently, the difference between $R(\Delta t)$ and $R(\Delta t')$ represents the precise relaxation process of the sample 19 with respect to the measured signal level after relaxation.

A delay-time-modulated pump probe measuring device related to a second embodiment of the present invention will be described below.

Figure 5:
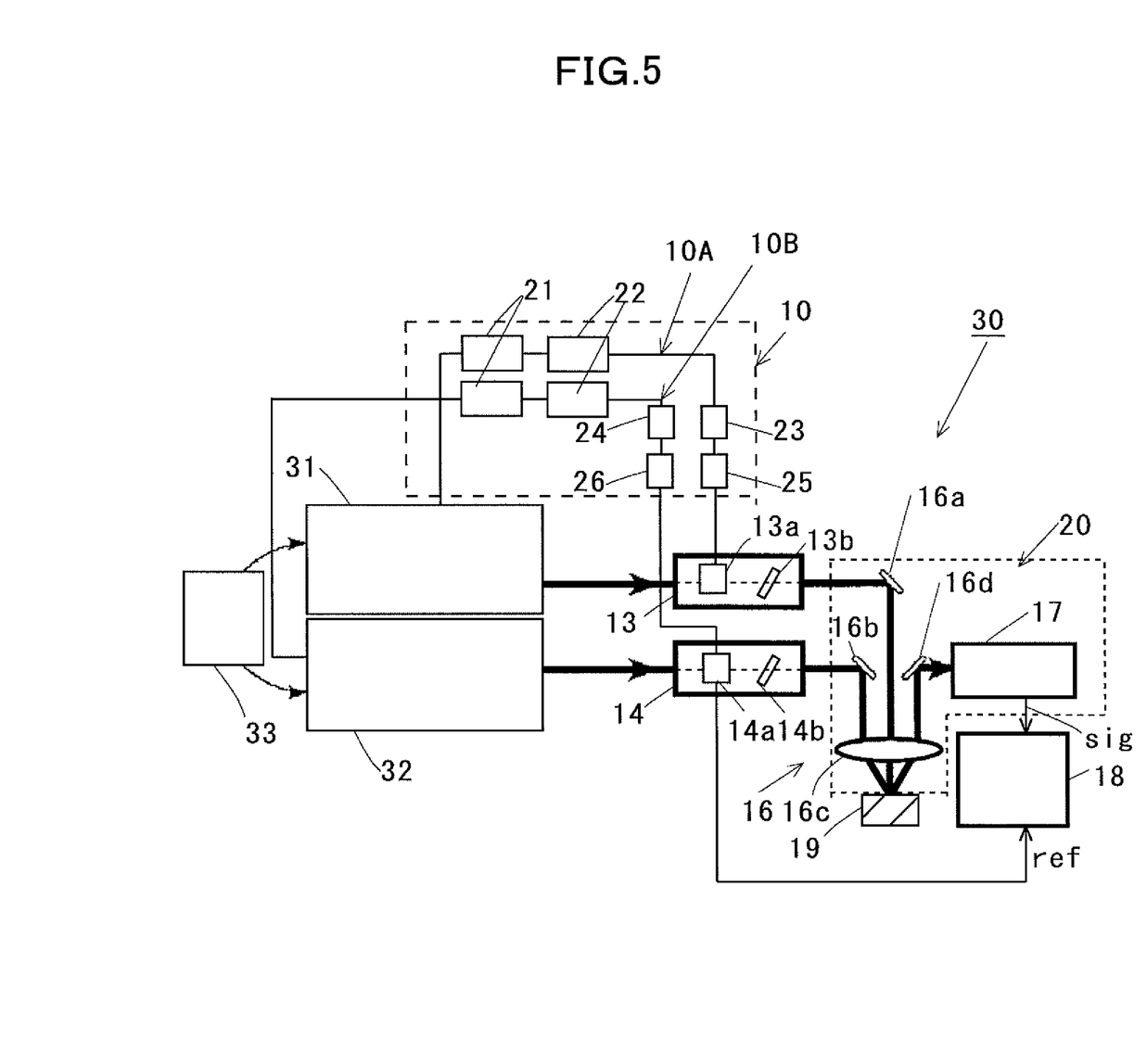
FIG. 5 is a block diagram illustrating the configuration of a second embodiment of a delay-time-modulated pump probe measuring device according to the present invention.

FIG. 5 illustrates the configuration of a delay-time-modulated pump probe measuring device in a second embodiment of the present invention. The delay-time-modulated pump probe measuring device 30 shown in FIG. 5 differs from the pump probe measuring device 1 as shown in FIG. 1 in that laser sources 31 and 32 are provided, instead of the laser source 11, for the pump light and the probe light respectively to eliminate the branch optical system 12 and the delay time adjusting unit 15, that a first pulse picker 13 is driven by a first delay time modulation unit 10A, and that a second pulse picker 13 is driven by a second delay time modulation unit 10B.

Each of the laser sources 31 and 32 has the same structure as the laser source 11 in the pump probe measuring device 1 in FIG. 1, and is controlled to oscillate at exactly the same periodicity by the operation of a synchronous oscillation control unit 33. Since there is no need to branch the incident light to introduce them to each pulse picker 13 and 14, the intensity of the pulse light applied to the sample 19 is enhanced. In addition, the delay time of the two laser pulses can be set freely by arbitrarily selecting the phase of the optical pulse to be output. Two ultrashort optical pulse laser sources 31 and 32 can be made to have identical wavelength. If their wavelengths differ from each other, the pump light and the probe light can have different wavelengths. Furthermore, by setting the oscillation phase of the pump light and the probe light as required using the synchronous oscillation control unit 33 for two laser devices, the delay time up to the repetition period can be set easily. Consequently, since the delay time can be adjusted using the two ultrashort optical pulse laser sources 31 and 32 and the two pulse pickers 13 and 14, the delay time adjusting unit 15, which is required when only one ultrashort optical pulse laser source is used, can be omitted. For example, if the titanium sapphire oscillators having repetition frequency of approximately 100 MHz are used as the laser sources 31 and 32, the synchronous oscillation control unit 33 allows the pump pulse light P1 and the probe pulse light P2 to be oscillated with the jitters of approximately 200 fs and with arbitrary delay time of up to the pulse repetition period.

Since the delay time between the pump pulse light P1 and the probe pulse light P2 can be set arbitrarily based on the operation of the synchronous oscillation control unit 33, the delay time adjusting unit 15 as shown in FIG. 1 can be omitted. The delay time setting range, which was approximately 1 ns at maximum with the pump probe measuring device 1 as shown in FIG. 1, can be extended up to the pulse repetition period, and at the same time, adverse effect such as slight deviation of optical axis due to transition of mirrors over a long distance, etc. can be eliminated. By adjusting the optical pulse transmission timing of the second pulse picker 14, the delay time can be set arbitrarily within the effective pulse repetition period after pulse picking, exceeding the base repetition period of the laser sources 31 and 32. This will allow measurement of relatively long relaxation time of several hundred nanoseconds to be conducted, even if laser sources 31 and 32 having repetition frequency of 100 MHz is used.

The first delay time modulation unit 10A includes: a photosensor 21 for detecting optical pulses generated by the first laser source 31 of the ultrashort optical pulse laser generator, a counting means 22 for counting pulse signals coming from the photosensor 21, a first delaying means 23 to be connected to the counting means 22, and a driving means 25 for driving the pulse picker 13. Likewise, the second delay time modulation unit 10B has a same configuration of the first delay time modulation unit 10A and it includes: a photosensor 21 for detecting optical pulses generated by the second laser source 32 of the ultrashort optical pulse laser generator, a counting means 22, a second delaying means 24, and a driving means 26 for driving the second pulse picker 14. Since the photosensor 21, the counting means 22, the first and the second delaying means 23 and 24, and the driving means 25 and 26 for the pulse pickers 13 and 14 can be structured in the same way as the delay time modulation unit 10 described by referring to FIG. 1, the description of these components will be omitted here. Installation of only one of the first and the second delaying means 23 and 24 is allowed.

According to the first and the second delay time modulation units 10A and 10B, the selection positions of the pulses passed by the pulse pickers 13 and 14 can be changed periodically, as in the case of the delay time modulation unit 10 as shown in FIG. 1.

The measuring device 30 in this configuration operates in the same way as the measuring device 1 as shown in FIG. 1. In this case, since two laser sources 31 and 32 are used, the equipment cost increases, and the accuracy of delay time setting tends to decrease compared with the measuring device 1 as shown in FIG. 1 due to the limitation imposed by the synchronous oscillation control unit 33. However, since the delay time setting can be made only by the synchronous oscillation control unit 33, the mechanism of mechanically moving the movable mirror 15a of the delay time adjusting unit 15 in FIG. 1 is not required. Consequently, the reliability of the measuring system and the stability of the focal point on the sample 19 improve significantly, which is the major advantage of this configuration.

A third embodiment of a delay-time-modulated pump probe measuring device related to the present invention will be described below.

Figure 6:
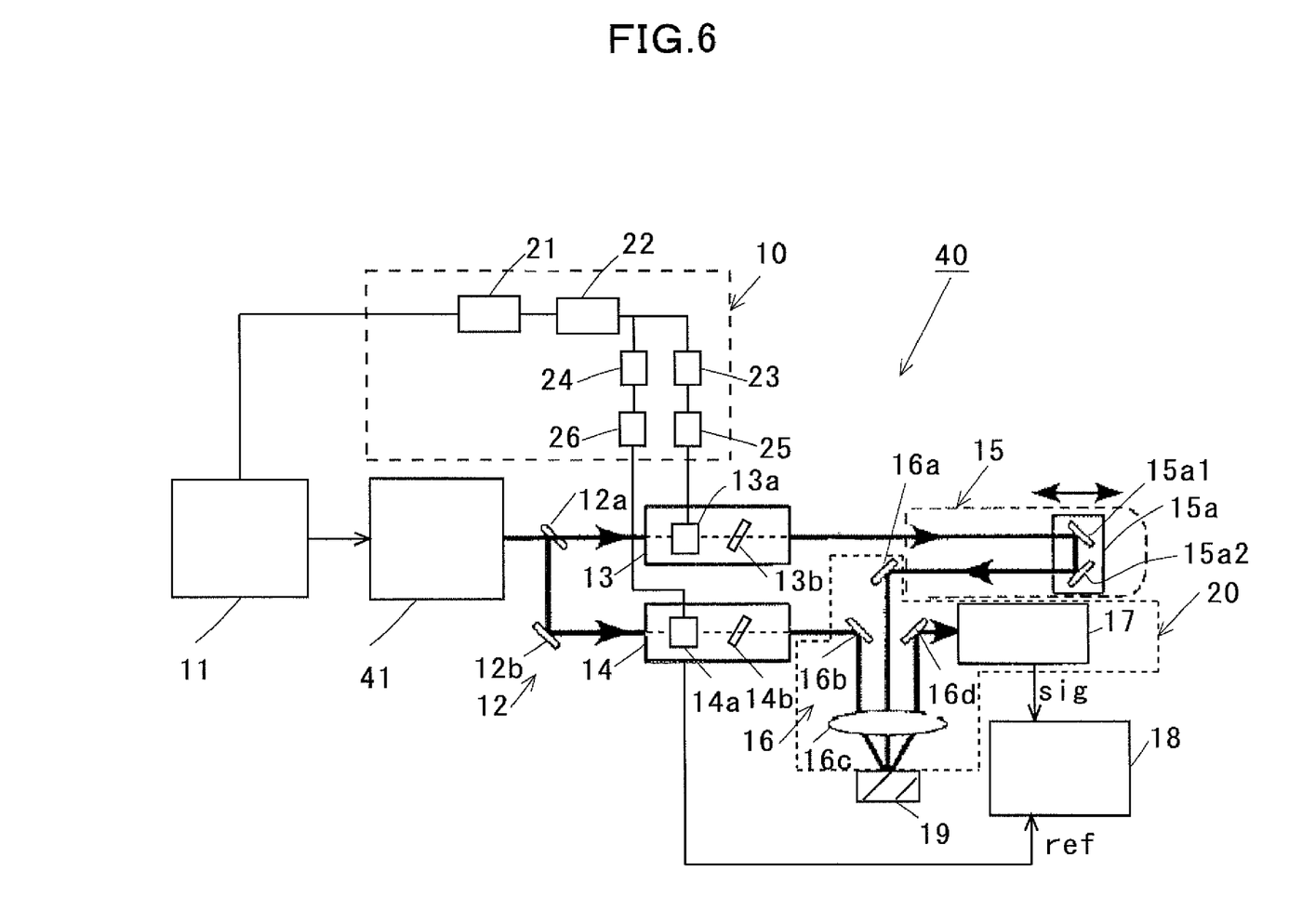
FIG. 6 is a block diagram illustrating the configuration of a third embodiment of a delay-time-modulated pump probe measuring device according to the present invention.

FIG. 6 illustrates the configuration of a delay-time-modulated pump probe measuring device in a third embodiment of the present invention. The delay-time-modulated pump probe measuring device 40 as shown in FIG. 6 differs from the pump probe measuring device 1 as shown in FIG. 1 in that a laser source 11 attached with a cavity dumper 41 is used instead of the laser source 11.

The laser source 11, 41 equipped with the cavity dumper has a known configuration. For example, a laser oscillator, where an acousto-optic modulator (AO modulator) is inserted into a cavity of a titanium sapphire laser, may be used. The highly intense optical pulse can be output at low repetition frequency by opening the cavity only once in several tens to several hundreds times of round trip movements in the cavity of the laser and by taking out an extremely intense laser pulse stored within the cavity, while maintaining the average intensity at approximately the same level as that of a conventional titanium sapphire laser oscillator. According to this configuration, a laser oscillator having the average intensity of several hundreds mW and repetition frequency of approximately 2 MHz can be achieved.

If Pockels cells having the maximum operating frequency of 1 MHz are used as the two pulse pickers 13 and 14 in the first and the second embodiments as shown in FIGS. 1 and 5, only one of 100 optical pulses generated from the laser oscillator can be transmitted. Consequently, the laser intensity decreases down to $1/100$. Even if the intensity of the laser from the laser sources 11, 31, and 32 is 1 W, the average intensity after passing the pulse pickers 13 and 14 decreases to approximately 10 mW.

On the contrary, in the embodiment as shown in FIG. 6, since the laser source 11, 41 has a repetition frequency of 2 MHz, for example, the pulse pickers 13 and 14 transmit one pulse in every two pulses output from the laser source 11, thus decreasing the repetition frequency from 2 MHz to 1 MHz and periodically changing the optical pulses to be transmitted. Thus, the delay time can be modulated as a rectangular waveform in the same manner as the embodiment as shown in FIG. 1.

The measuring device 40 in this configuration operates in the same manner as the measuring device 1 as shown in FIG. 1, with the decrease of average intensity at the pulse pickers 13 and 14 maintained at approximately 50%. Probe light signal intensity much higher than that of the embodiment shown in FIG. 1 can thus be obtained.

Each embodiment described above assumes the case in which the reflectance of the sample was measured by the rectangular-wave pump probe modulation method. In addition to these methods, an arbitrary time-resolved pump probe measurement method can be combined with the rectangular-wave delay time modulation method using pulse pickers. Consequently, capitalizing on the feature of the present invention that measurement can be made over a wide delay time range without modifying the intensity of pump probe light, a microscope apparatus capable of measuring ultrafast phenomena that occur in submicroscopic space can be achieved in combination with a scanning tunneling microscope.

A scanning probe microscope apparatus using a delay-time-modulated pump probe measuring device as a fourth embodiment of the present invention will be described below.

Figure 7:
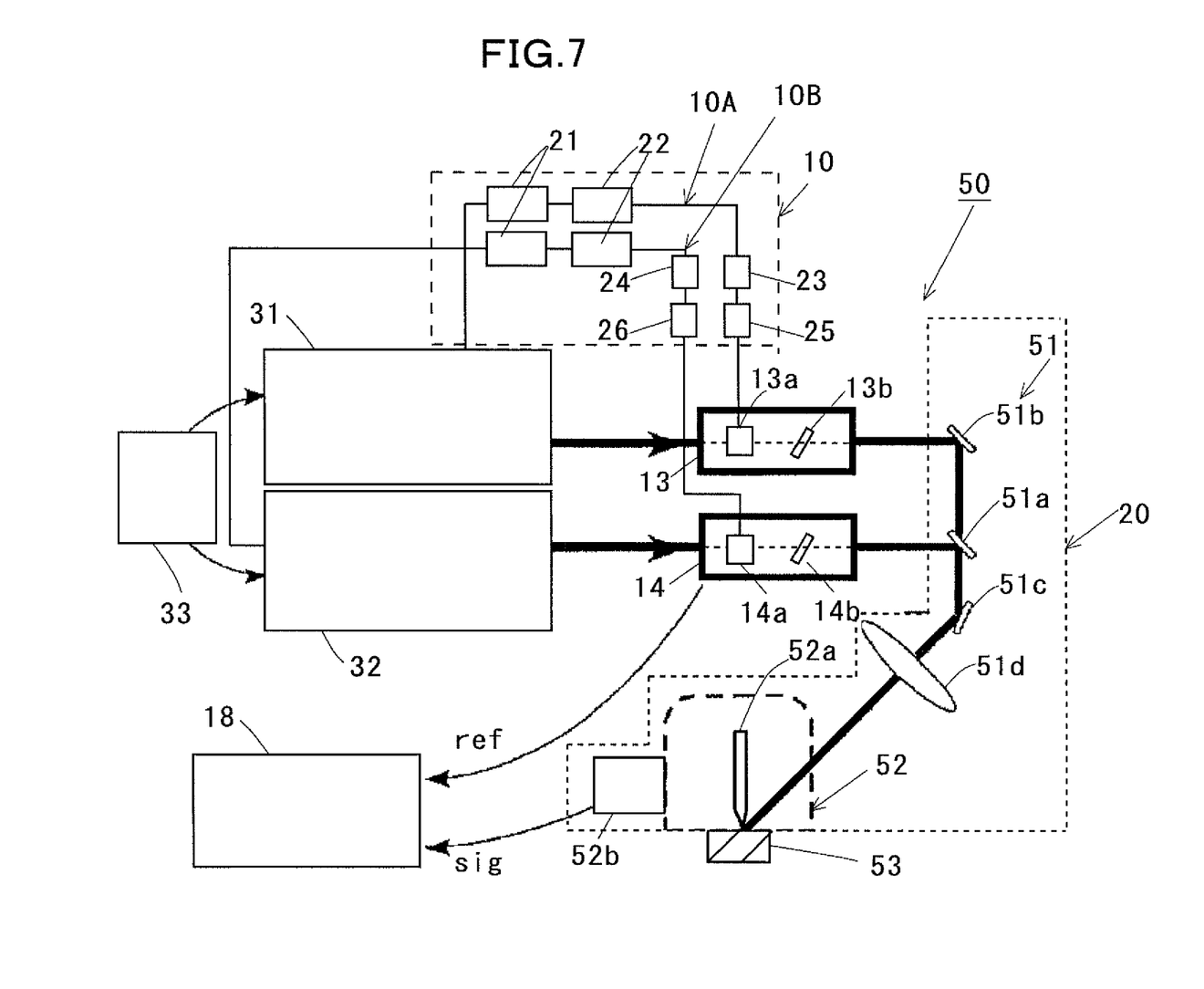
FIG. 7 is a block diagram illustrating the configuration of an embodiment of a delay-time-modulated scanning probe microscope apparatus having a time resolution of the order of femtosecond according to the present invention.

FIG. 7 is a block diagram illustrating the configuration of one of the embodiments of a delay-time-modulated scanning probe microscope apparatus having a time resolution of the order of femtosecond according to the present invention. A scanning probe microscope apparatus 50 in FIG. 7 includes two laser sources 31 and 32, a synchronous oscillation control unit 33, a delay time modulation unit 10, a first pulse picker 13 and a second pulse picker 14, an irradiation optical system 51, a scanning tunneling microscope 52, and a lock-in amplifier 18.

As shown in FIG. 7, the scanning probe microscope apparatus 50 according to the fourth embodiment of the present invention differs from the pump probe measuring device according to the second embodiment of the present invention as shown in FIG. 5 in that a measuring unit 20 is equipped with the irradiation optical system 51 and the scanning tunneling microscope 52.

The irradiation optical system 51 includes a half mirror 51a, two reflecting mirrors 51b and 51c, and an objective lens 51d. The pump pulse light coming from the first pulse picker 13 is reflected by the reflecting mirror 51b, transmitted through the half mirror 51a, further reflected by the reflecting mirror 51c, and focused on a surface of a sample 53 in the scanning tunneling microscope 52 via the objective lens 51d. The probe pulse light coming from the second pulse picker 14 is reflected by the half mirror 51a, overlapped with the pump pulse on the same optical axis, further reflected by the reflecting mirror 51c, and focused on the surface of the sample 53 in the scanning tunneling microscope 52 via the objective lens 51d.

The scanning tunneling microscope 52 is a well-known configuration provided with a probe 52a immediately above the surface of the sample 53 to allow a tunnel junction to be formed between the apex of the probe 52a and the sample 53. The probe 52a is scanned on the surface of the sample 53. By applying laser pulses to the surface of the sample 53, probe signals generated by modulating the tunneling current between the apex of the probe 52a and the sample 53 are detected by a preamplifier 52b for current detection, and the amplified signal is output to the lock-in amplifier 18.

According to the microscope 50 having the above configuration, laser pulses coming from the laser sources 31 and 32 are applied to the sample 53 placed immediately beneath the probe 52a, via the pulse pickers 13 and 14, and then via the irradiation optical system 51, as the pump pulse light and the probe pulse light respectively. In this case, pairs of laser pulses having delay time set by the synchronous oscillation control unit 33 and the pulse pickers 13 and 14 excite the surface of the sample 53. At that time, to maintain the tunneling current between the probe 52a and the sample 53 at a constant level, the scanning tunneling microscope 52 adjusts the gap between the probe 52a and the sample 53 by the feedback control having a low cutoff frequency.

When the pulse pickers 13 and 14 are driven by the driving means 25 and 26 to modulate the delay time, in order to avoid signals targeted for measurement being attenuated by the feedback control circuit, the modulation frequency of the pump pulse light is kept sufficiently higher than the cutoff frequency of the feedback control of the scanning tunneling microscope 52. In this state, when the output signals coming from the preamplifier 52b for current detection of the scanning tunneling microscope 52 is detected by the lock-in amplifier 18, which is a phase sensitive detection, with respect to the modulation frequency of the second pulse picker 14, the ultrafast physical phenomenon occurring in submicroscopic space on the surface of the sample 53 placed immediately beneath the probe 52a can be observed as the output signals.

EXAMPLES

Examples of the delay-time-modulated pump probe measuring device according to the present invention will be described below.

The basic principle of the measurement procedure of the delay-time-modulated pump probe measuring device according to the present invention is the same as that of the widely used conventional delay-time-modulated pump probe measuring device, but innovative improvement has been made to the modulation method. Even if such improvement is made, the system operates normally based on the basic operation principle governing the conventional systems.

Of the embodiments shown above, the configuration of the scanning probe microscope apparatus 50 as shown in FIG. 7 will be described in details below.

The ultrafast time-resolved scanning tunneling microscope 50 is composed by combining the rectangular-wave-based delay time modulation system using pulse pickers, which is the core of the present invention, and the conventional scanning tunneling microscope.

First, the typical configuration of a conventional device used for the same purpose will be described. As in the case of the measuring unit 20 as shown in FIG. 7, since the pump pulse light and the probe pulse light of the conventional device are also applied to the sample on the identical optical axis, the sample is excited repeatedly by pulse pairs consisting of two optical pulses, namely the pump and the probe pulses. It is the reason why this type of microscope is called the pulse-pair-excited time-resolved scanning tunneling microscope. A delay-time-modulated optical pulse-pair-excited scanning tunneling microscope apparatus is known as a typical conventional device that mechanically oscillates the position of mirrors included in a delay time setting optical system to perform delay time modulation. When the sample placed under the scanning tunneling microscope is excited using pulse pairs that have been delay-time-modulated by mirror oscillation, a subpicosecond or several tens picosecond ultrafast phenomena occurring in a submicroscopic region of the order of nanometer can be measured. With the conventional device of this type, however, the delay time modulation amplitude is small and the modulation frequency is low, which tends to lower the signal-noise ratio. Consequently, there was a drawback that a single measurement required as long as several hours to several tens hours.

The microscope apparatus 50 according to the embodiment of the present invention as shown in FIG. 7 also employs the configuration of the optical pulse-pair-excited scanning tunneling microscope as in the case of a conventional device. Since the delay time modulation system is improved as described above, the signal intensity can be increased by raised modulation amplitude, the noise intensity can be decreased by raised modulation frequency, the time resolution is not negatively affected by the modulation amplitude, and the deviation of the focal point of the laser from the position of the probe of the scanning tunneling microscope due to long-distance mirror transfer can be avoided.

As a laser source 31 in FIG. 7, CHAMELEON by COHERENT INC., and as the laser source 32, MIRA also by COHERENT, are used. These two laser sources 31 and 32 are capable of independently generating approximately 150 fs laser pulses at 90 MHz repetition frequency and average output power of 0.3 to 1.5 W for 750 nm to 950 nm arbitrary wavelengths, respectively. The laser sources 31 and 32 are allowed to oscillate synchronously at the jitter of approximately 500 fs by using synchro-lock controller by COHERENT as a synchronous oscillation control unit 33. Furthermore, since the timing with respect to the phase of oscillation can be arbitrary selected under the condition that the oscillation intervals are fully synchronized, the delay time can be set arbitrary over the entire pulse repetition period without externally setting a delay time adjusting unit 15 employing long-distance movable mirror transfer mechanism.

Pockels cells (RTP-3-20 by Laysop Ltd.) 13a and 14a were used as the first and the second pulse pickers 13 and 14, respectively. The switching time of each pulse pickers 13 and 14 was approximately 1 ns, and the maximum repetition frequency was 1.5 MHz. One pulse can be picked up out of approximately 100 pulses from 90 MHz pulse lasers generated by the laser sources 31 and 32. Pockels cell drivers 25 and 26 (High Repetition-Rate Pockels Cell Driver by ME) 25 and 26 were used as drive sources for driving these Pockels cells 13a and 14a. The combination of these Pockels cell drivers 25 and 26 and the Pockels cells (RTP-3-20) 13a and 14a ensures repetition frequency of 1 MHz, which is appropriate for the embodiment of the present invention.

The laser beam intensity immediately before the entry to the pulse pickers 13 and 14 was detected by the fast photo diode 21 having a frequency band width of approximately 1 GHz to determine the driving timing of the pulse pickers 13 and 14.

Detected intensity was used as clock signals to operate the delay time modulation unit 10 including the CPLD, which is a programmable integrated circuit, thus generating signals for controlling the Pockels cell drivers 25 and 26, the driving means of the Pockels cells 13a and 14a of the pulse pickers 13 and 14. Specifically, by transmitting one pulse out of every 90 pulses, the laser pulse repetition frequency after transmission is set to 1 MHz. In addition, the driving timing of the second pulse picker 14 only is modulated by a half cycle (0.5 μs) at the modulation frequency of approximately 1 to 2 kHz.

Here, the modulation frequency must be sufficiently lower than the bandwidth (up to tens of kHz) of the current detection preamplifier 52b of the scanning tunneling microscope 52 on the latter stage, and sufficiently higher than the weak feedback bandwidth (up to 10 Hz) applied to the distance between the probe 52a of the scanning tunneling microscope 52 and the sample 53. Consequently, the modulation frequency of approximately 1 to 2 kHz is appropriate. Generally, when the phase-sensitive detection is performed on tunneling current signals of the scanning tunneling microscope, it is advantageous to set high modulation frequency in order to avoid the noise due to the mechanical vibration. Since the modulation frequency selected here, 1 to 2 kHz, is 50 to 100 times higher than 20 Hz of the conventional delay-time-modulated system employing mechanical mirror transfer method, the noise level will be minimized to ⅕ to 1/10. Furthermore, by increasing the modulation amplitude, which used to be 0.5 to 1 ps, up to approximately 0.5 μs, the signal level is expected to increase to 10 times as high or higher. With both combined, the signal noise ratio is expected to become several tens to several hundreds times higher.

The pump pulse light and the probe pulse light that have passed through the pulse pickers 13 and 14 are overlapped on the same optical axis by the half mirror 51a and reflecting mirrors 51b, 51c of the irradiation optical system 51, and then introduced to the scanning tunneling microscope 52 via the objective lens 51d. The diameter of the focal point of the laser beam on the surface of the sample 53 should remain as small, and the distance from the objective lens 51d to the focal point on the surface of the sample as long, as possible, by using a composite optical system consisting of multiple lenses as the objective lens 51d. Specifically, the beam diameter is expanded to 3 to 5 cm using a concave lens first, and then it is narrowed down using a convex lens. This is a simple method producing good results.

This allows the focal point diameter to be as small as several μm even when the distance from the objective lens 51d to the sample 51 is increased to approximately 300 mm. This design is necessary to obtain sufficient light intensity while avoiding physical interference between the scanning tunneling microscope 52 and the objective lens 51d, and to minimize the disturbance in measurement due to thermal expansion and contraction of the probe 52a, when the apparatus is used in combination with a microscope capable of obtaining measurements in a vacuum environment, in particular.

As the scanning tunneling microscope 52, a type capable of carrying out measurement in an ultrahigh vacuum environment is used to observe the surface of semiconductors, for example. Normally, the ultrahigh vacuum scanning tunneling microscope employs a vibration-free structure by suspending a detector unit with a soft spring within the vacuum to prevent imperceptible vibration of the floor from being transmitted to the measuring device.

However, in implementing the present invention, if the positional relation between the laser optical system for generating delay-time-modulated pulse pairs and the detecting unit of the scanning tunneling microscope deviates significantly, the relative position of the sample 53, or probe 52a, and the focus of the objective lens 51d, namely the irradiation position of the excitation light source also deviates, thus adversely affecting measurement. It is therefore preferable that the laser optical system and the scanning tunneling microscope be placed on a large single vibration-isolating board to minimize vibration coming from floor surface and maintain proper mechanical and positional relation between them.

Results of measurement performed using the scanning probe microscope apparatus 50 in the above example will be described below.

As the sample 53 targeted for measurement, a $GaN_xAs_{1-x}$ (composition x here is 0.36%) thin film grown on a GaAs wafer at low temperature by the molecular beam epitaxy method (MBE) was cleaved on a (110) face, and its cross-sectional area was used for measurement. Since the growth temperature of this sample was low, its defect density was high. This defect plays a major role in recombination of photo-carrier, and consequently, the fast photocarrier relaxation process of approximately several tens picoseconds to several hundreds picoseconds is expected.

Figure 8:
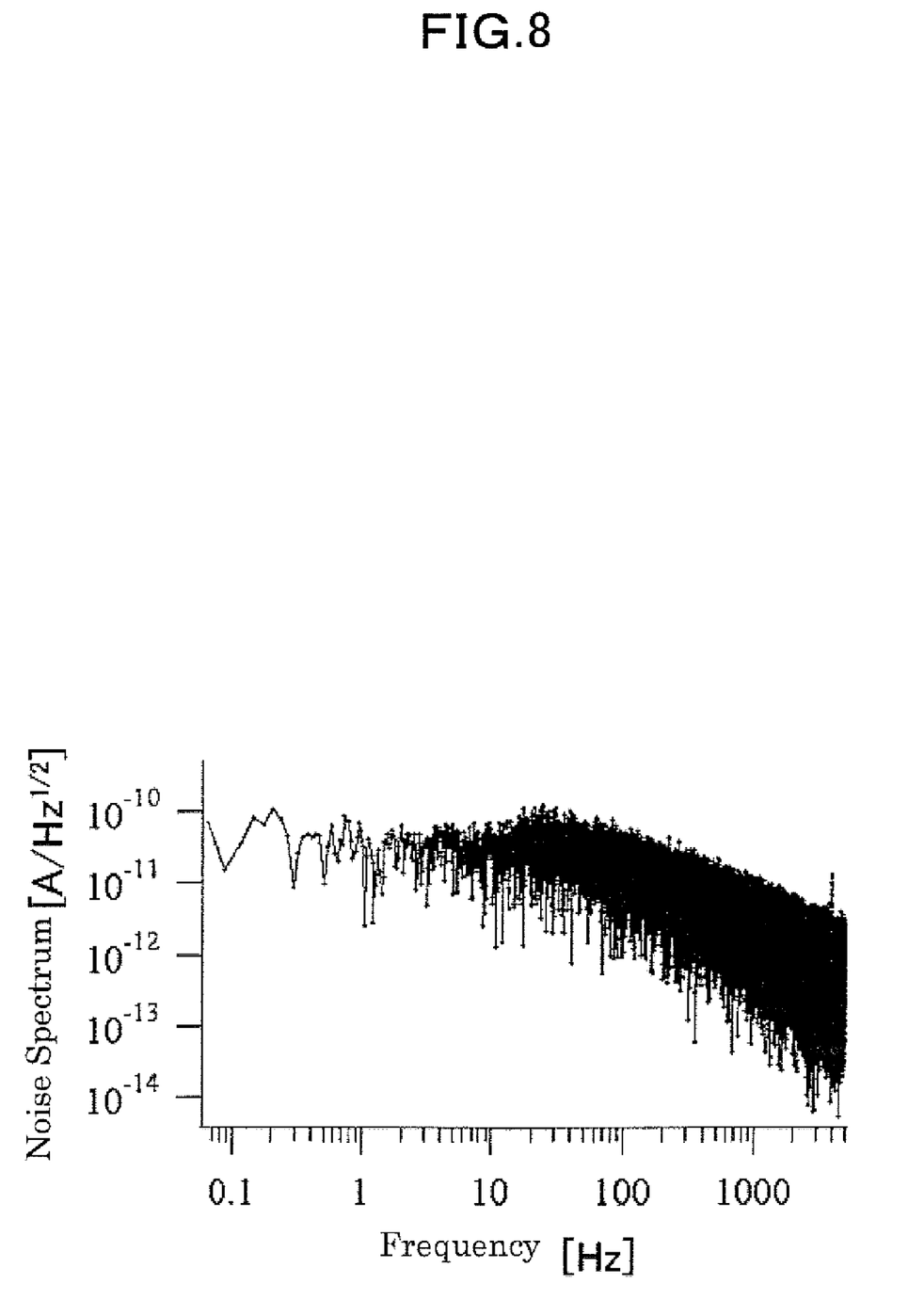
FIG. 8 is a chart illustrating a noise spectrum of tunneling current signals measured by a current-voltage conversion preamplifier of a scanning tunneling microscope of a scanning probe microscope apparatus in the embodiment as shown in FIG. 7.

FIG. 8 is a chart illustrating a noise spectrum of tunneling current signals measured by the current-voltage conversion preamplifier 52b of the scanning tunneling microscope 52 of the scanning probe microscope apparatus 50 in the embodiment as shown in FIG. 7. In FIG. 8, the abscissa axis indicates frequency (Hz), whereas the ordinate axis indicates noise spectrum ($A/Hz^{1/2}$).

As is obvious from FIG. 8, the noise density around 1 kHz modulation frequency in delay time modulation using pulse pickers in the scanning probe microscope apparatus 50 in this example is approximately 1/10 of the noise density around 20 Hz modulation frequency, which is used for a conventional delay-time-modulated scanning tunneling microscope 52 employing mechanical mirror vibration. It was thus confirmed that the increased modulation frequency would decrease the noise level significantly.

Figure 9:
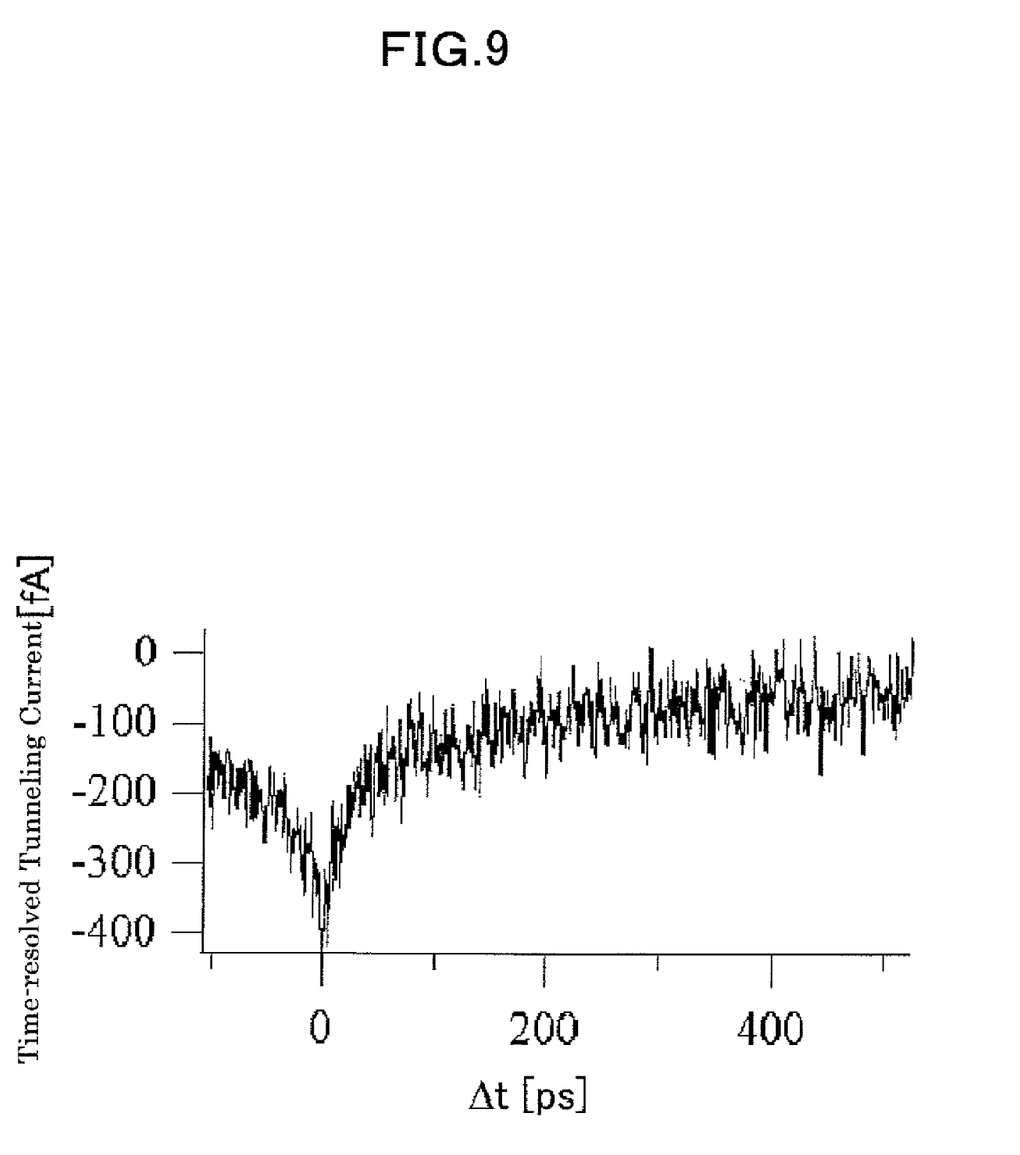
FIG. 9 is a chart illustrating a time-resolved tunneling current of a low-temperature-grown $GaN_xAs_{1-x}$ thin film measured under a scanning probe microscope apparatus in the Example.

FIG. 9 is a chart illustrating a time-resolved tunneling current of a low-temperature-grown $GaN_xAs_{1-x}$ thin film sample measured under a scanning probe microscope apparatus 50 in the example. In FIG. 9, the output from the lock-in amplifier 18 is illustrated as the function of Δt (ps) as shown in FIG. 2, and the ordinate axis indicates time-resolved tunneling current (fA). In this case, Δt' in FIG. 2 was assumed to be approximately 0.5 μs.

As described previously, the output signal from the lock-in amplifier 18 represents delay-time-dependent component I (Δt) of the tunneling current value itself for sufficiently large Δt', reflecting ultrafast response in a nm-scale submicroscopic region immediately beneath the probe 52a of the scanning tunneling microscope 52 placed on the sample 53, mostly the relaxation process of the photocarrier. As is obvious from FIG. 9, the ultrafast relaxation process that occurs in several tens or several hundreds picoseconds can be detected as a change in femtoampere (fA) order tunneling current. It was found that the signal noise ratio at this time was approximately 100 times higher than that of conventional devices.

INDUSTRIAL APPLICABILITY

The present invention significantly improves the delay time modulation method of the conventional delay-time-modulated pump probe measurement method, which has thus far been used widely. From the perspective that the application of ultrafast phenomena will become increasingly important in the future, the present invention is of great significance and its scope of application is extremely wide. In the pump light intensity modulation, for example, sample temperature fluctuates significantly, thus adversely affecting measurement results. However, by using the method achieved by the present invention, the measurements can be performed with the sample temperature kept almost constant.

A femtosecond time-resolved scanning probe microscope according to the present invention is expected to ensure the signal noise ratio approximately 100 times higher than that of conventional microscopes. Since the measurement can be made while a temperature of the sample is maintained at approximately the same level, dramatic development is expected. For example, a carrier lifetime and carrier transfer in a picosecond region within semiconductor nano-devices can be measured, and means of measurement thus far unavailable will be provided. Gaining deeper understanding of new physical phenomena capitalizing on the present invention would be of significant importance in the research phase of devices providing new functions. The wide scope of application of the present invention also includes on-site use for evaluating fabricated devices.

The pump probe device of the present invention can also be used as various types of measuring apparatus, attached to measuring devices such as scanning electron microscope and transmission electron microscope.

What is claimed is:

1. A pump probe measuring device comprising:
    an ultrashort optical pulse laser generator for generating a first ultrashort optical pulse train, which becomes a pump light, and a second ultrashort optical pulse train, which becomes a probe light;
    a delay time adjusting unit for adjusting a delay time of said first and second ultrashort optical pulse trains;
    a first pulse picker and a second pulse picker for reducing effective repetition frequency of optical pulses by accepting each of said first and second ultrashort optical pulse trains and transmitting only one pulse at an arbitrary repetition frequency;
    a delay time modulating unit for periodically changing a position through which optical pulses are transmitted by said first and second pulse pickers;
    a measuring unit for detecting probe signals from a sample equipped with an irradiation optical system for applying said pump light and said probe light to said sample; and
    a lock-in detecting unit for performing a phase-sensitive detection of probe signals from said sample at a modulation frequency of said delay time modulation unit, wherein
    the first or the second pulse picker changes the position through which optical pulses are transmitted, thus changing the delay time between the optical pulse that is transmitted through said second pulse picker or the optical pulse that is transmitted through said first pulse picker.

2. The pump probe measuring device as set forth in claim 1, wherein each pulse picker comprises a Pockels cell and a light polarizer, and it transmits or blocks arbitrary optical pulses.

3. The pump probe measuring device as set forth in claim 1 or 2, wherein said delay time modulation unit comprises: a photosensor for detecting optical pulses generated by said ultrashort optical pulse laser generator; a counting means for counting pulse signals from said photosensor; a delaying means to be connected to said counting means; and a driving means for said pulse pickers.

4. The pump probe measuring device as set forth in claim 1, wherein said ultrashort optical pulse laser generator includes a laser source comprising a titanium sapphire laser.

5. The pump probe measuring device as set forth in claim 1, wherein an optical system employing an optical path length adjustment mechanism using movable mirrors is provided with said delay time adjusting unit.

6. The pump probe measuring device as set forth in claim 1 or 4, wherein said ultrashort optical pulse laser generator comprises: an ultrashort optical pulse laser source; and an optical device for dividing the ultrashort optical pulses generated by said ultrashort optical pulse laser source to form the pump light and the probe light.

7. The pump probe measuring device as set forth in claim 1, wherein said ultrashort optical pulse laser generator comprising two ultrashort optical pulse laser sources and the ultrashort optical pulses generated by each ultrashort optical pulse laser source are transmitted into the corresponding pulse pickers as the pump light and the probe light, respectively.

8. The pump probe measuring device as set forth in claim 6 or 7, wherein a cavity dumper is provided with said ultrashort optical pulse laser source.

9. The pump probe measuring device as set forth in claim 1, wherein an optical system for applying the pump light and the probe light to the surface of the sample and an optical system for measuring the intensity of said reflected probe light is provided with said measuring unit, and said intensity of the reflected probe light is output as probe signals.

10. A scanning probe microscope apparatus comprising a pump probe measuring device as set forth in any one of claims 1 to 9, wherein a scanning tunneling microscope for measuring local physical properties at the position where pump light and probe light are applied is provided with said measuring unit, and the probe signals obtained by said scanning tunneling microscope are output.

11. Various measuring devices including a pump probe measuring device as set forth in any one of claims 1 to 9 as one of their components.

* * * * *